(12) United States Patent
Nakao et al.

(10) Patent No.: US 8,637,480 B2
(45) Date of Patent: Jan. 28, 2014

(54) MITOCHONDRIAL FUNCTION-IMPROVING AGENT

(75) Inventors: Mitsuyoshi Nakao, Kumamoto (JP);
Shinjiro Hino, Kumamoto (JP)

(73) Assignee: National University Corporation Kumamoto University, Kumamoto (JP)

( * ) Notice: Subject to any disclaimer, the term of this patent is extended or adjusted under 35 U.S.C. 154(b) by 0 days.

(21) Appl. No.: 13/263,391

(22) PCT Filed: Mar. 29, 2010

(86) PCT No.: PCT/JP2010/002271
§ 371 (c)(1),
(2), (4) Date: Jan. 9, 2012

(87) PCT Pub. No.: WO2010/116673
PCT Pub. Date: Oct. 14, 2010

(65) Prior Publication Data
US 2012/0108648 A1    May 3, 2012

(30) Foreign Application Priority Data

Apr. 10, 2009 (JP) .................. 2009-095544

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ................ 514/44 A; 536/24.5

(58) Field of Classification Search
USPC ................ 514/44; 536/24.5
See application file for complete search history.

(56) References Cited

U.S. PATENT DOCUMENTS

2007/0208082 A1   9/2007 Woster et al.

FOREIGN PATENT DOCUMENTS

| EP | 1 693 062 A2 | 8/2006 |
| JP | 2009-509922 | 3/2009 |
| WO | 2006/138475 | 12/2006 |

OTHER PUBLICATIONS

Extended European Search Report issued with respect to patent family member EP Patent Application No. 10761379.6, dated Feb. 18, 2013.
Balasubramaniyan et al., "Regulation of Peroxisome Proliferator-Activated Receptor Gamma Coactivator 1α(PGC-1α) by Lysine Specific Demethylasel (LSD1)-Mediated Lysine Demethylation and its Implications for FXR Transactivation in Liver" *Hepatology* vol. 50, No. S4, p. 624A, 2009.
Balasubramaniyan et al., "Regulation of Peroxisome Proliferator-Activated Receptor Gamma Coactivator 1α (PGC-1α) by Lysine Specific Demethylasel (LSD1)-Mediated Lysine Demethylation and its Implications for FXR Transactivation in Liver" *Hepatology* vol. 50, No. S4, p. 624A, 2009.
Hino et al., "Epigenetic Regulation of Energy Metabolism by the Histone Demethylase, LSD1", Dai 82 Kai The Japanese Biochemical Society Taikai Program, Koen Yoshishu, Sep. 25, 2009, vol. 82, p. 3S17A-5.

(Continued)

*Primary Examiner* — Terra Cotta Gibbs
(74) *Attorney, Agent, or Firm* — Greenblum & Bernstein, P.L.C.

(57) ABSTRACT

It is an object of the present invention to provide a novel mitochondrial function-improving agent and a novel PGC-1α expression inducing agent. The present invention provides a mitochondrial function-improving agent and a PGC-1α expression inducing agent each of which comprises a lysine-specific demethylase-1 (LSD-1) inhibitor.

6 Claims, 14 Drawing Sheets

(56) References Cited

OTHER PUBLICATIONS

Han et al., "Antidepressants Reveal Differential Effect Against 1-Methyl-4-Phenylpyridinium Toxicity in Differentiated PC12 Cells" *European Journal of Pharmacology* vol. 604, No. 1-3, pp. 36-44, 2009.

Schmidt et al., "*trans*-2-Phenylcyclopropylamine Is a Mechanism-Based Inactivator of the Histone Demethylase LSD1" *Biochemistry* vol. 46, No. 14, pp. 4408-4416, 2007.

Lee et al., "Histone H3 Lysine 4 Demethylation Is a Target of Nonselective Antidepressive Medications" *Chemistry and Biology* vol. 13, pp. 563-567, 2006.

International Search Report for PCT/JP2010/002271 mailed Apr. 27, 2010, along with an English language translation.

International Preliminary Report on Patentability for PCT/JP2010/002271 dated Dec. 22, 2010, along with an English language translation.

Canadian Office Action issued with respect to Canadian Patent App. No. 2,761,634, dated Oct. 22, 2013.

Data 2

SEQUENCE LISTING

```
<160> NUMBER OF SEQ ID NOS: 42

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagtgtggaa ctctctggaa ctg                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggttatctt ggttggcttt atg                                            23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caaggagatc tgaatctcta                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gataatgttt gaaggctgac                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aactgatgag cagagatgcc                                                20
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aacatggcat ccagaacttg                                                20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgcccaggac tctgcaaag                                                 19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cacagaagtc tggactggga                                                20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcccttgta aacaacaaaa tac                                            23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcaacaaga gctgacagta aat                                            23

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgtcctggc attgtctgt                                                 19

<210> SEQ ID NO 12
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcaaatgcag atggatcagc c                                              21

<210> SEQ ID NO 13
<211> LENGTH: 19
<212> TYPE: DNA
<213> ORGANISM: Mus sp.

<400> SEQUENCE: 13
cacaaggaaa gctagaaga                                                 19

<210> SEQ ID NO 14
<211> LENGTH: 19
<212> TYPE: DNA
<213> ORGANISM: Mus sp.

<400> SEQUENCE: 14
gttccagata cagccattg                                                 19

<210> SEQ ID NO 15
<211> LENGTH: 19
<212> TYPE: DNA
<213> ORGANISM: Mus sp.

<400> SEQUENCE: 15
tcttccagct gatgtgtgt                                                 19

<210> SEQ ID NO 16
<211> LENGTH: 19
<212> TYPE: DNA
<213> ORGANISM: Mus sp.

<400> SEQUENCE: 16
gagcccttgg aggaatgtc                                                 19

<210> SEQ ID NO 17
<211> LENGTH: 19
<212> TYPE: DNA
<213> ORGANISM: Mus sp.

<400> SEQUENCE: 17
gatttcgagt cgtcttaat                                                 19

<210> SEQ ID NO 18
<211> LENGTH: 19
<212> TYPE: DNA
<213> ORGANISM: Mus sp.

<400> SEQUENCE: 18
ctggacttcc agaagaaca                                                 19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 19
gtctaattga gactggctgt g                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caacatgttg agcaactcag c                                              21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aagcttgact ggcgtcattc                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctccggtcc tgcaatactc                                                20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcaaagatgc ctcctgtgac                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caaggagaga cctgcttgct                                                20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```

```
ctggctagga atgcgtgaca                                                       20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gatcccaggt cgctaggact                                                       20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgcccaggac tctgcaaag                                                        19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cacagaagtc tggactggga                                                       20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 29
cacaaggaaa gcuagaagat t                                                     21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 30
ucuucuagcu uuccuugugt t                                                     21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued

```
                transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 31
guuccagaua cagccauugt t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 32
caauggcugu aucuggaact t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 33
ucuuccagcu gaugugucut t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 34
agacacauca gcuggaagat t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 35
gagcccuugg aggaauguct t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 36
gacauuccuc caagggcuct t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 37
gauuucgagu cgucuuaaut t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 38
auuaagacga cucgaaauct t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 39
cuggacuucc agaagaacat t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      transcribed RNA oligonucleotide
<220> FEATURE:
<223> OTHER INFORMATION: Description of Combined DNA/RNA Molecule:
      Synthetic transcribed RNA oligonucleotide

<400> SEQUENCE: 40
uguucuucug gaaguccagt t                                              21

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic

```
        peptide

<400> SEQUENCE: 41

Gly Ser Gly Val Ser Gly
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 42

Gly Ser Ala Val Ser Ala
1               5
```

MITOCHONDRIAL FUNCTION-IMPROVING AGENT

SEQUENCE LISTING

The instant application contains a Sequence Listing which has been submitted in ASCII format via EFS-Web and is hereby incorporated by reference in its entirety. Said ASCII copy, created on Jan. 5, 2012, is named P40878.txt and is 10,803 bytes in size.

TECHNICAL FIELD

The present invention relates to a mitochondrial function-improving agent and a PGC-1α expression inducing agent, each of which comprises a lysine-specific demethylase-1 (LSD-1) inhibitor.

BACKGROUND ART

Energy metabolism in mitochondria plays an essential role not only for the maintenance of life but also for various high-order functions. It has been known that a decrease in mitochondrial function induces many disorders in tissues that demand for high energy, such as brain and muscle. On the other hand, the regulation of such mitochondrial function strongly depends on the expression control of a metabolizing enzyme gene by intranuclear transcription factors. Among others, a decrease in the function of a transcription regulatory factor PGC-1α that plays an integrative role causes mitochondria-related diseases.

Tranylcypromine is one type of monoamine oxidase inhibitor, which has an activity to inhibit the action of monoamine oxidase, so as to increase substances in the brain, such as dopamine. The tranylcypromine has been known to be effective as an antidepressant. Patent Document 1 describes a metabolic syndrome therapeutic agent which contains tranylcypromine. Non Patent Document 1 describes that tranylcypromine inhibits LSD1 enzyme. Non Patent Document 2 describes that other monoamine oxidase inhibitors have low LSD1 inhibitory activity.

PRIOR ART DOCUMENTS

Patent Document

Patent Document 1: WO2006/138475

Non Patent Documents

Non Patent Document 1: Schmidt, D. M., and McCafferty, D. G. (2007). Trans-2-Phenylcyclopropylamine is a mechanism-based inactivator of the histone demethylase LSD1. Biochemistry 46, 4408-4416.

Non Patent Literature 2: Lee, M. G., Wynder, C., Schmidt, D. M., McCafferty, D. G., and Shiekhattar, R. (2006). Histone H3 lysine 4 demethylation is a target of nonselective antidepressive medications. Chemistry and Biology. 13, 563-567.

SUMMARY OF INVENTION

Object to be Solved by the Invention

It is an object to be solved by the present invention to provide a novel mitochondrial function-improving agent and a novel PGC-1α expression inducing agent.

Means for Solving the Object

As a result of intensive studies directed towards achieving the aforementioned object, the present inventor has discovered that histone demethylase LSD1 suppresses the expression of a mitochondrial function gene including PGC-1α. In addition, the inventor has found that tranylcypromine acting as an LSD1 inhibitor and LSD1 or BHC80 gene specific RNAi are able to induce the expression of PGC-1α, and are able to activate energy metabolism in mitochondria. Moreover, the inventor has also found that an LSD1 target gene group including PGC-1α is induced by inhibition of synthesis of flavin adenosine dinucleotide (FAD). From these results, it became clear that LSD1 function inhibition is effective for the improvement of mitochondrial function. The present invention has been completed based on these findings.

Specifically, the present invention provides the following features of the invention.

(1) A mitochondrial function-improving agent which comprises a lysine-specific demethylase-1 (LSD-1) inhibitor.

(2) The mitochondrial function-improving agent according to (1) above, wherein the lysine-specific demethylase-1 (LSD-1) inhibitor is tranylcypromine; a nucleic acid capable of suppressing the expression of LSD1 or BHC80 or an enzyme associated with FAD synthesis by RNAi; or a FAD synthesis inhibitor.

(3) The mitochondrial function-improving agent according to (2) above, wherein the enzyme associated with FAD synthesis is riboflavin kinase (RFK) and/or FAD synthase (FADS).

(4) The mitochondrial function-improving agent according to any one of (1) to (3) above, wherein the nucleic acid capable of suppressing the expression of LSD1 by RNAi is siRNA consisting of the sequence shown in SEQ ID NO: 29 and siRNA consisting of the sequence shown in SEQ ID NO: 30.

(5) A PGC-1α expression inducing agent which comprises a lysine-specific demethylase-1 (LSD-1) inhibitor.

(6) The PGC-1α expression inducer according to (5) above, wherein the lysine-specific demethylase-1 (LSD-1) inhibitor is tranylcypromine; a nucleic acid capable of suppressing the expression of LSD1 or BHC80 or an enzyme associated with FAD synthesis (riboflavin kinase (RFK), FAD synthase (FADS), etc.) by RNAi; or a FAD synthesis inhibitor.

(7) The PGC-1α expression inducer according to (6) above, wherein the enzyme associated with FAD synthesis is riboflavin kinase (RFK) and/or FAD synthase (FADS).

(8) The PGC-1α expression inducer according to any one of (5) to (7) above, wherein the nucleic acid capable of suppressing the expression of LSD1 by RNAi is siRNA consisting of the sequence shown in SEQ ID NO: 29 and siRNA consisting of the sequence shown in SEQ ID NO: 30.

Advantageous Effects of Invention

LSD 1 is a chromatin structure regulatory protein that has been recently identified, and many of its physiological roles are still unknown. In the present invention, it was found that LSD1 controls mitochondrial function via regulation of a PGC-1α gene expression. Other than the present method, there have been reported no methods of targeting a specific chromatin regulatory factor to improve mitochondrial function. According to the present invention, a novel therapeutic target can be developed. It can be anticipated that the agent of the present invention can be used in the molecular target treatment of diseases associated with a decrease in mitochondrial function (cranial nerve disease, myopathy, heart disease, etc.).

BRIEF DESCRIPTION OF DRAWINGS

FIG. 11 discloses the "hLSD1 wt" and "hLSD1 mut" peptides as SEQ ID NOS 41 & 42, respectively.

EMBODIMENTS OF CARRYING OUT THE INVENTION

Figure 1:
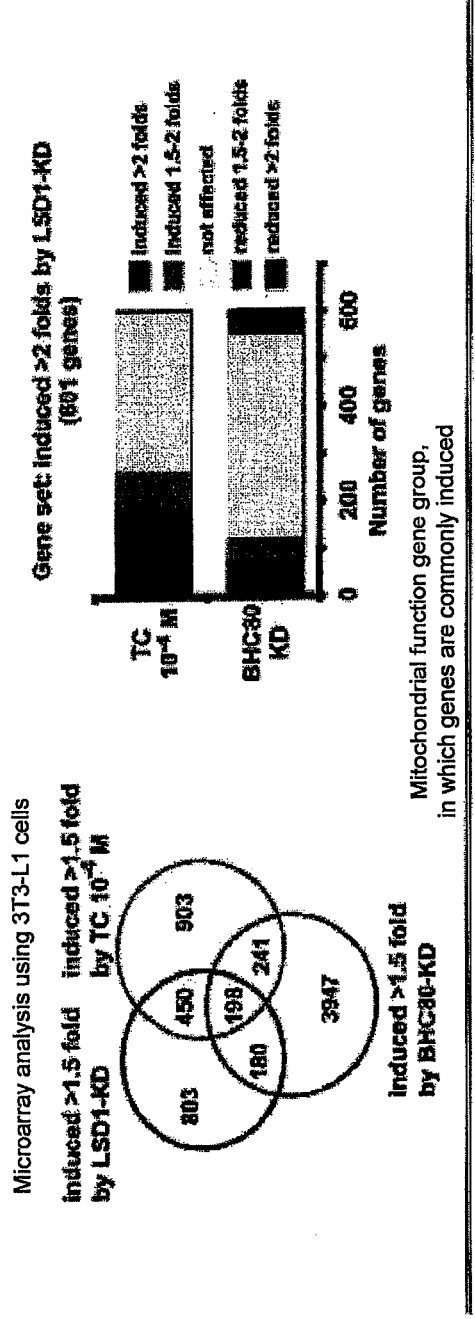
FIG. 1 shows the results of a comprehensive search of LSD1 target genes in 3T3-L1 cells, using RNAi to LSD1, RNAi to BHC80 that is an essential cofactor for LSD1 function, or tranylcypromine (TC).

The present invention will be described more in detail below.

The present invention relates to a mitochondrial function-improving agent and a PGC-1α expression inducing agent, each of which comprises a lysine-specific demethylase-1 (LSD-1) inhibitor. In the present invention, the improvement of mitochondrial function means an increase in the amount of mitochondria and/or activation of a citric acid cycle, a fatty acid β oxidation system, an electron transfer system, etc.

The type of the lysine-specific demethylase-1 (LSD-1) inhibitor used in the present invention is not particularly limited, as long as it is a substance capable of inhibiting the function of lysine-specific demethylase-1 (LSD1). Examples of such a lysine-specific demethylase-1 (LSD-1) inhibitor include tranylcypromine and a nucleic acid capable of suppressing the expression of LSD1 by RNAi. In addition, RNAi to a coupling factor of LSD1 (BHC80, etc.) or an enzyme associated with FAD synthesis necessary for LSD1 enzyme activity can also be used. A FAD synthesis inhibitor comprising a FAD analogue, a low molecular weight compound or the like can also be used.

The nucleic acid capable of suppressing the expression of LSD1 by RNAi includes siRNA and shRNA, which will be described below. If such a factor is introduced into a cell, an RNAi phenomenon occurs, and RNA having a homologous sequence is decomposed. This RNAi phenomenon is observed in nematodes, insects, protozoa, hydra, plants, and vertebrate animals (including mammals).

In a preferred embodiment, a double stranded RNA called siRNA, which has a length of approximately 20 nucleotides (for example, approximately 21 to 23 nucleotides) or less than 20 nucleotides, can be used in the present invention. When such siRNA is allowed to express in a cell, it suppresses gene expression, so that it is able to suppress the expression of a target gene thereof (which is an LSD1 gene in the present invention).

The form of the siRNA used in the present invention is not particularly limited, as long as it can cause RNAi. The term "siRNA" is used herein as an abbreviation of short interfering RNA. The siRNA means a short-chain double-stranded RNA consisting of 10 or more base pairs, which is artificially chemically synthesized, or is biochemically synthesized, or is synthesized in an organism, or is formed by decomposing double-stranded RNA consisting of approximately 40 or more nucleotides in a body. In general, the siRNA has such a structure as 5'-phosphate or 3'-OH, and its 3'-terminus protrudes by approximately 2 nucleotides. A specific protein binds to this siRNA to form RISC (RNA-induced-silencing-complex). This complex recognizes mRNA having the same sequence as that of siRNA and binds thereto, and it then cleaves the mRNA by RNaseIII-like enzyme activity at the center of the siRNA.

The sequence of siRNA is preferably 100% identical to the sequence of RNA to be cleaved as a target. However, in a case in which nucleotides located apart from the center of the siRNA are not identical, cleaving activity caused by RNAi partially remains. Thus, the two above sequences are not necessarily 100% identical to each other.

A homologous region between the nucleotide sequence of siRNA and the nucleotide sequence of an LSD1 gene, the expression of which is to be suppressed, preferably does not contain the translation initiation region of the LSD1 gene. This is because since it is anticipated that various transcriptional factors or translational factors bind to the translation initiation region, siRNA cannot effectively bind to mRNA, and thus it is anticipated that the obtained effects are reduced. Accordingly, the homologous region is apart from the translation initiation region of the LSD1 gene preferably by 20 nucleotides, and more preferably by 70 nucleotides. The homologous sequence may be a sequence around the 3'-terminus of the LSD1 gene, for example.

In the present invention, siRNA can be used as a factor that causes RNAi, and a factor that generates siRNA (for example, dsRNA consisting of approximately 40 or more nucleotides) can also be used as the aforementioned factor. There can be used, for example, RNA containing a double-stranded portion, which comprises a sequence showing homology of at least approximately 70%, preferably 75% or more, more preferably 80% or more, further preferably 85% or more, still further preferably 90% or more, particularly preferably 95% or more, and most preferably 100% with a portion of the nucleic acid sequence of the LSD1 gene, or a modified body thereof. A homologous sequence portion has a nucleotide length consisting of generally at least approximately 15 nucleotides or more, preferably at least 19 nucleotides, more preferably at least approximately 20 nucleotides, and further preferably at least approximately 21 nucleotides.

A specific example of siRNA that can be used in the present invention is a double-stranded RNA consisting of RNA having the nucleotide sequence shown in SEQ ID NO: 29 and RNA having the nucleotide sequence shown in SEQ ID NO: 30. However, examples of siRNA are not limited thereto. It is to be noted that the nucleotide sequence of the LSD1 gene is publicly known and that it has been registered under NCBI accession No. NM 015013, for example.

In another embodiment of the present invention, as a factor capable of suppressing the expression of LSD1 by RNAi, there can be used shRNA (short hairpin RNA) consisting of a short hairpin structure having a protrusion portion at the 3'-terminus thereof. The term "shRNA" is used to mean RNA molecules consisting of approximately 20 or more base pairs, in which single-stranded RNA partially contains a palindromic nucleotide sequence and it thereby adopts a double-stranded structure in the molecule thereof, so as to have a hairpin-like structure. When such shRNA is introduced into a cell, it is decomposed into a length of approximately 20 nucleotides (as representative examples, 21 nucleotides, 22 nucleotides, or 23 nucleotides) in the cell, and it can cause RNAi, as in the case of siRNA. As stated above, since shRNA can cause RNAi as in the case of siRNA, it can be effectively used in the present invention.

shRNA preferably has a 3'-protruding end. The length of a double-stranded portion is not particularly limited. It is preferably about 10 or more nucleotides, and more preferably about 20 or more nucleotides. Herein, the 3'-protruding end is preferably DNA, more preferably DNA consisting of at least 2 nucleotides, and further preferably DNA consisting of 2 to 4 nucleotides.

The factor capable of suppressing the expression of LSD1 by RNAi that is used in the present invention (namely, the above-described siRNA or shRNA, etc.) may be artificially chemically synthesized. Alternatively, it may also be produced by synthesizing RNA in vitro from DNA having a hairpin structure, in which the DNA sequence of a sense strand is ligated to the DNA sequence of an antisense strand in the reverse direction, using T7 RNA polymerase. In the case of the in vitro synthesis, antisense and sense RNA portions can be synthesized from template DNA using T7 RNA polymerase and a T7 promoter. These RNAs are annealed in vitro, and the double-stranded product is then introduced into a cell. As a result, RNAi is induced, and the expression of LSD1 is thereby suppressed. Herein, such RNA can be introduced into a cell, for example, by applying a calcium phosphate method or using various types of transfection reagents (for example, oligofectamine, lipofectamine, lipofection, etc.).

The mitochondrial function-improving agent and PGC-1α expression inducing agent of the present invention may be administered via oral administration or parenteral administration (for example, intravenous administration, intramuscular administration, subcutaneous administration, intracutaneous administration, mucosal administration, intrarectal administration, intravaginal administration, local administration to an affected area, skin application, etc.).

When the mitochondrial function-improving agent and PGC-1α expression inducing agent of the present invention are used as pharmaceutical compositions, pharmaceutically acceptable additives can be added thereto, as necessary. Specific examples of such pharmaceutically acceptable additives include, but are not limited to, an antioxidant, a preservative, a coloring agent, a flavoring agent, a diluent, an emulsifier, a suspending agent, a solvent, a filler, a thickener, a buffer, a delivery vehicle, a diluent, a carrier, an excipient and/or a pharmaceutical adjuvant.

The dosage forms of the mitochondrial function-improving agent and PGC-1α expression inducing agent of the present invention are not particularly limited. Examples of the dosage form include a liquid agent, an injection, and a sustained release agent. The solvent used to formulate the above-described pharmaceutical agents from the mitochondrial function-improving agent and PGC-1α expression inducing agent of the present invention may be either an aqueous solvent or a non-aqueous solvent.

The injection can be prepared by a method well known in the present technical field. For example, the mitochondrial function-improving agent or PGC-1α expression inducing agent of the present invention is dissolved in a suitable solvent (a normal saline, a buffer such as PBS, a sterilized water, etc.), and the obtained solution is then sterilized by filtration with a filter or the like. Subsequently, the thus sterilized solution is filled into an aseptic container (for example, an ample, etc.) so as to prepare an injection. This injection may comprise a commonly used pharmaceutical carrier, as necessary. An administration method using a noninvasive catheter can also be used. Examples of the carrier that can be used in the present invention include a neutral buffered normal saline, and a normal saline mixed with serum albumin.

The applied doses of the mitochondrial function-improving agent and PGC-1α expression inducing agent of the present invention can be determined by a person skilled in the art, while taking into consideration intended use, the severity of disease, the age, body weight, sex and anamnesis of a patient, the type of a nucleic acid capable of suppressing the expression of LSD1 by RNAi that is used as an active ingredient, and the like. In the case of tranylcypromine, it can be administered within the dose range of, for example, 1 mg to 100 mg, and preferably 10 mg to 100 mg per adult per day. In the case of using a substance capable of suppressing the expression of LSD1 by RNAi as an active ingredient, the applied dose is not particularly limited. It is, for example, approximately 0.1 ng/kg to approximately 100 mg/kg, and preferably approximately 1 ng to approximately 10 mg per day.

The present invention will be more specifically described in the following examples. However, these examples are not intended to limit the scope of the present invention.

EXAMPLES (A) Methods
(1) Comprehensive Analysis of LSD1 Target Genes in 3T3-L1 Cells, Using Microarray (FIG. 1)

Figure 2:
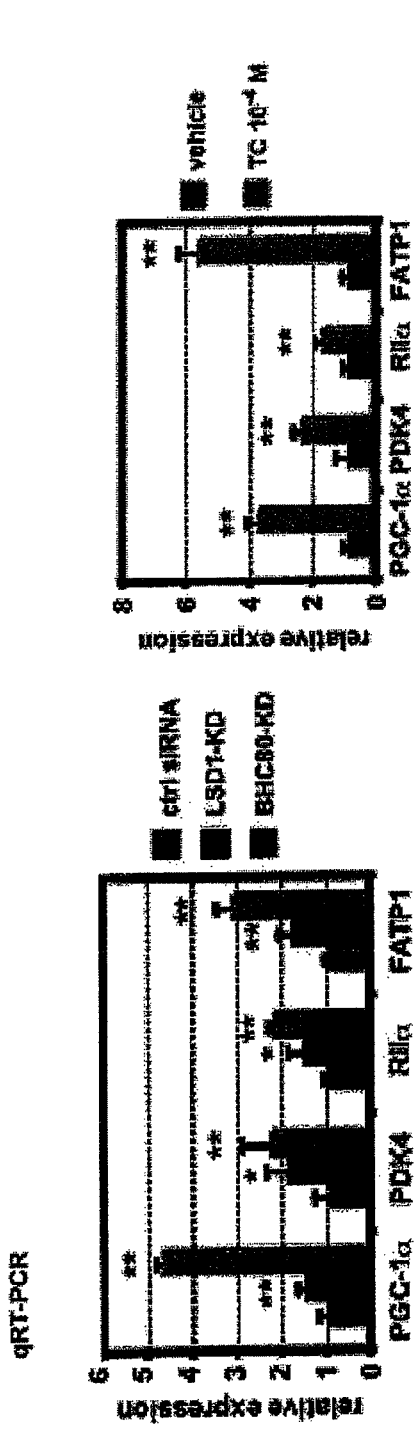
FIG. 2 shows the results of induction of the expression of a mitochondrial function gene group including PGC-1α by inhibition of LSD1.

After completion of introduction of siRNA to LSD1 or BHC80 as a coupling factor thereof using RNAimax reagent (Invitrogen), or addition of $10^{-4}$ M tranylcypromine-HCl (TC, Sigma), 3T3-L1 cells were cultured in a differentiation induction medium for 24 hours, and RNA analysis was then carried out. An adipogenesis induction medium was prepared by dissolving 0.5 μM 3-isobutyl-1-methylxanthine, 1 μM dexamethasone and 5 μg/ml insulin in a Dulbecco's modified Eagle's medium containing 10% fetal bovine serum. Total RNA was extracted using RNeasy mini column (Qiagen). Using GeneChip Mouse Genome Array 430_2 in combination with GeneChip Hybridization, Wash and Stain Kit (Affymetrix), genome-wide expression analysis was carried out
(2) Expression Analysis of PGC-1α gene and the Like by Quantitative Real-time PCR (FIG. 2)

Total RNA was extracted using Trizol reagent (Invitrogen). Quantitative RT-PCR was carried out using Fast SYBR Green System (Applied Biosciences). The expression level of PGC-1α or the like was standardized against an internal control gene 36B4. The value is given as a multiple of induction to a sample into which control siRNA has been introduced or a sample treated with a vehicle. Statistical significant difference is indicated by *$p<0.05$, **$p<0.01$, with respect to control (the same applies below). The following primers were used.

```
                                         (SEQ ID NO: 1)
PGC-1α/forward:  5'-AAGTGTGGAACTCTCTGGAACTG-3'

(SEQ ID NO: 2)
PGC-1α/reverse:  5'-GGGTTATCTTGGTTGGCTTTATG-3'

(SEQ ID NO: 3)
PDK4/forward:  5'-CAAGGAGATCTGAATCTCTA-3'

(SEQ ID NO: 4)
PDK4/reverse:  5'-GATAATGTTTGAAGGCTGAC-3'

(SEQ ID NO: 5)
RIIα/forward:  5'-AACTGATGAGCAGAGATGCC-3'

(SEQ ID NO: 6)
RIIα/reverse:  5'-AACATGGCATCCAGAACTTG-3'

(SEQ ID NO: 7)
FAT1P/forward:  5'-CGCCCAGGACTCTGCAAAG-3'

(SEQ ID NO: 8)
FATP1/reverse:  5'-CACAGAAGTCTGGACTGGGA-3'

(SEQ ID NO: 9)
UCP1/forward:  5'-GGCCCTTGTAAACAACAAAATAC-3'

(SEQ ID NO: 10)
UCP1/reverse:  5'-GGCAACAAGAGCTGACAGTAAAT-3'

(SEQ ID NO: 11)
36B4/forward:  5'-GCGTCCTGGCATTGTCTGT-3'

(SEQ ID NO: 12)
36B4/forward:  5'-GCAAATGCAGATGGATCAGCC-3'
```

Target sequences of siRNAs are as follows.

```
                                         (SEQ ID NO: 13)
LSD1:  5'-CACAAGGAAAGCTAGAAGA-3'

(SEQ ID NO: 14)
BHC80:  5'-GTTCCAGATACAGCCATTG-3'

(SEQ ID NO: 15)
RFK:  5'-TCTTCCAGCTGATGTGTGT-3'

(SEQ ID NO: 16)
FADS:  5'-GAGCCCTTGGAGGAATGTC-3'

Control siRNA
                                         (SEQ ID NO: 17)
GL3:  5'-GATTTCGAGTCGTCTTAAT-3'

(SEQ ID NO: 18)
lamin A/C:  5'-CTGGACTTCCAGAAGAACA-3'
```

The above-described siRNAs have the following sequences.

```
LSD1 sense:
                                         (SEQ ID NO: 29)
5'-CACAAGGAAAGCUAGAAGA(dT)(dT)-3'

LSD1 antisense:
                                         (SEQ ID NO: 30)
5'-UCUUCUAGCUUUCCUUGUG(dT)(dT)-3'

BHC80 sense:
                                         (SEQ ID NO: 31)
5'-GUUCCAGAUACAGCCAUUG(dT)(dT)-3'

BHC80 antisense:
                                         (SEQ ID NO: 32)
5'-CAAUGGCUGUAUCUGGAAC(dT)(dT)-3'

RFK sense:
                                         (SEQ ID NO: 33)
5'-UCUUCCAGCUGAUGUGUCU(dT)(dT)-3'

RFK antisense:
                                         (SEQ ID NO: 34)
5'-AGACACAUCAGCUGGAAGA(dT)(dT)-3'

FADS sense:
                                         (SEQ ID NO: 35)
5'-GAGCCCUUGGAGGAAUGUC(dT)(dT)-3'

FADS antisense:
                                         (SEQ ID NO: 36)
5'-GACAUUCCUCCAAGGGCUC(dT)(dT)-3'

GL3 sense:
                                         (SEQ ID NO: 37)
5'-GAUUUCGAGUCGUCUUAAU(dT)(dT)-3'

GL3 antisense:
                                         (SEQ ID NO: 38)
5'-AUUAAGACGACUCGAAAUC(dT)(dT)-3' lamin A/C sense:
                                         (SEQ ID NO: 39)
5'-CUGGACUUCCAGAAGAACA (dT)(dT)-3' lamin A/C antisense:
                                         (SEQ ID NO: 40)
5'-UGUUCUUCUGGAAGUCCAG(dT)(dT)-3'
```

Figure 3:
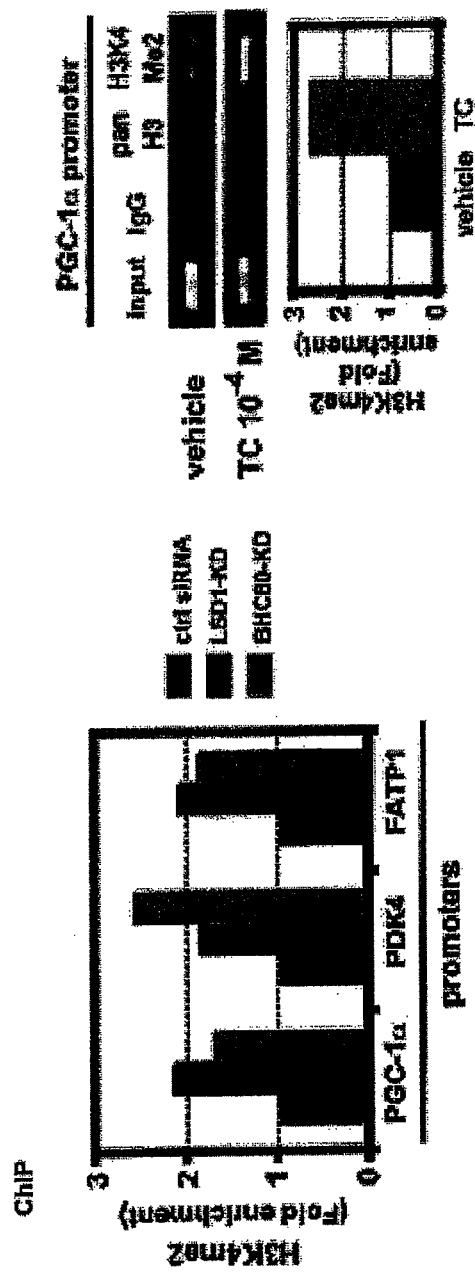
FIG. 3 shows the results of an analysis of histone methylation in 3T3-L1 cells by inhibition of LSD1 according to chromatin immunoprecipitation (ChIP).
Figure 4:
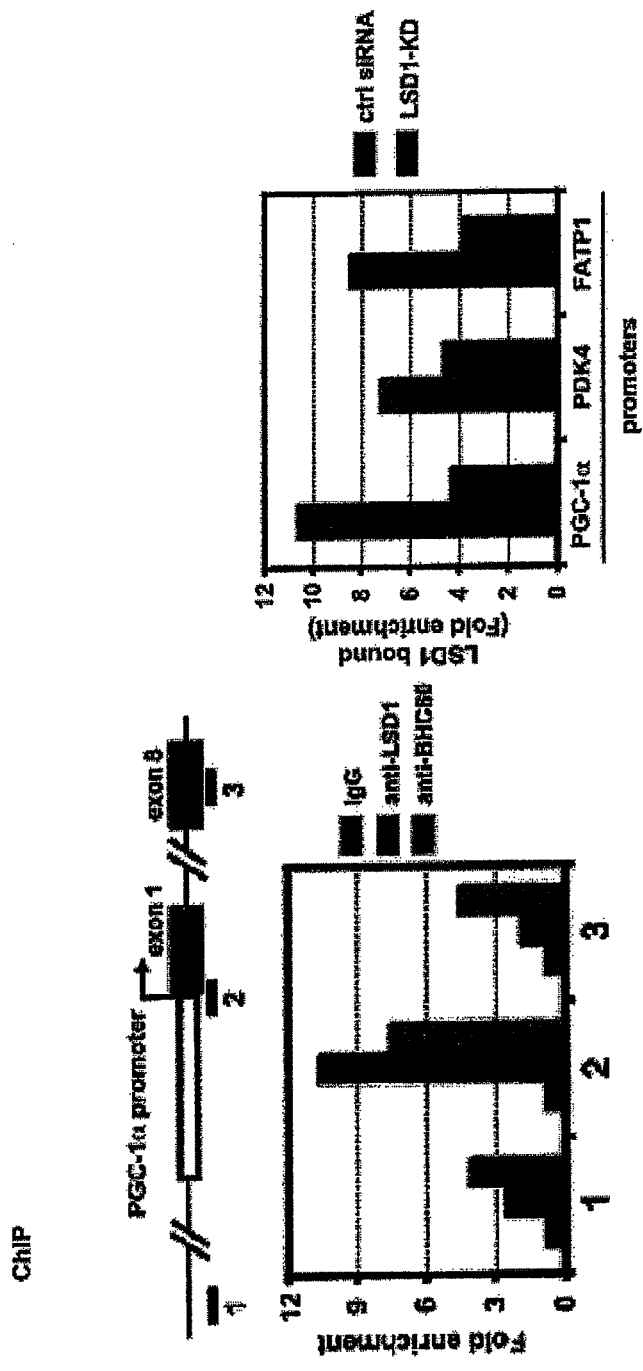
FIG. 4 shows the results of quantification of LSD1/promoter interaction in 3T3-L1 cells according to chromatin immunoprecipitation (ChIP).

(3) Chromatin Immunoprecipitation (ChIP) Assay for Detecting Methylation of $4^{th}$ Lysine Residue of Histone H3 (H3K4) and Binding of LSD1 (FIG. 3 and FIG. 4)

A DNA-protein complex of 3T3-L1 cells was crosslinked using 1% formalin, and chromatin was then fragmented using a water tank ultrasonic processor. The chromatin fragments were incubated at 4° C. overnight in the presence of an antibody directed against methyl-H3K4, LSD1 or BHC80. Thereafter, the reaction product was recovered using agarose beads to which protein A and protein G had been bound. DNA was isolated, and real-time PCR was then carried out using the following primer set PGC-1a Gene Loci

```
                                         (SEQ ID NO: 19)
Region a: forward:  5'-GTCTAATTGAGACTGGCTGTG-3'

(SEQ ID NO: 20)
Region a: reverse:  5'-CAACATGTTGAGCAACTCAGC-3'

(SEQ ID NO: 21)
Region b: forward:  5'-AAGCTTGACTGGCGTCATTC-3'

(SEQ ID NO: 22)
Region b: reverse:  5'-GCTCCGGTCCTGCAATACTC-3'

(SEQ ID NO: 23)
Region c: forward:  5'-TCAAAGATGCCTCCTGTGAC-3'

(SEQ ID NO: 24)
Region c: reverse:  5'-CAAGGAGAGACCTGCTTGCT-3'
```

-continued

PDK4: forward: 5'-CTGGCTAGGAATGCGTGACA-3' (SEQ ID NO: 25)

PDK4: reverse: 5'-GATCCCAGGTCGCTAGGACT-3' (SEQ ID NO: 26)

FATP1: forward: 5'-CGCCCAGGACTCTGCAAAG-3' (SEQ ID NO: 27)

FATP1: reverse: 5'-CACAGAAGTCTGGACTGGGA-3' (SEQ ID NO: 28)

Figure 5:
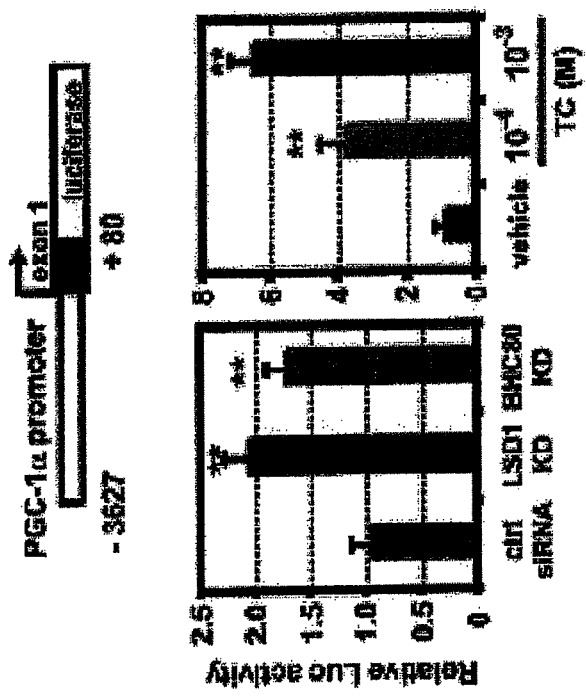
FIG. 5 shows the results of evaluation of PGC-1α promoter activity by inhibition of LSD1 according to luciferase assay.

(4) Analysis of PGC-1α Promoter Activity by Luciferase Assay (FIG. 5)

In order to construct pGL3-PGC-1α (PGC-1α/Luc) that is a luciferase reporter vector containing an mPGC-1α promoter, a 3707 bps promoter fragment from −3627 to +80 was amplified by PCR, using primers containing a MluI site and a XhoI site at the 5'-terminus and 3'-terminus thereof, respectively. Luciferase assay was carried out using Dual-Luciferase Reporter Assay System (Promega) in accordance with protocols included therewith. 3T3-L1 cells were co-transfected with the pGL3-PGC-1α reporter vector and a pRL-TK reference vector, and adipose differentiation was induced in the presence or absence of TC for 24 hours. Thereafter, luciferase activity was measured. When siRNA was applied, it was introduced 24 hours before transfection with the reporter.

(5) Evaluation of Mitochondrial Biosynthesis in 3T3-L1 Cells Treated with Tranylcypromine (TC) (FIG. 6)

For the measurement of mitochondrial biosynthesis, cells were stained with a fluorescent dye JC-1 (Molecular Probes), and they were then analyzed by flow cytometry. JC-1 binds to the mitochondrial inner membrane to emit green fluorescence, and forms a red fluorescent aggregate, depending on membrane potential. Accordingly, the amount of mitochondria can be evaluated by detecting the green fluorescence, whereas the amount of mitochondrial electron transport can be evaluated by detecting the red fluorescence. 3T3-L1 cells were treated with $10^{-3}$ or $10^{-4}$ M tranylcypromine (FIG. 6a), or the above-described siRNA against LSD1 was introduced therein (FIG. 6b), so that adipose differentiation was then induced for 24 hours. Subsequently, the cells were allowed to come into contact with 5 μg/ml JC-1 in a medium at 37° C. for 15 minutes, and they were then suspended in PBS, followed by FACS analysis. The green fluorescence and the red fluorescence were detected by FL1 and FL2 settings, respectively. The value indicates a mean fluorescence intensity in each setting.

Figure 7:
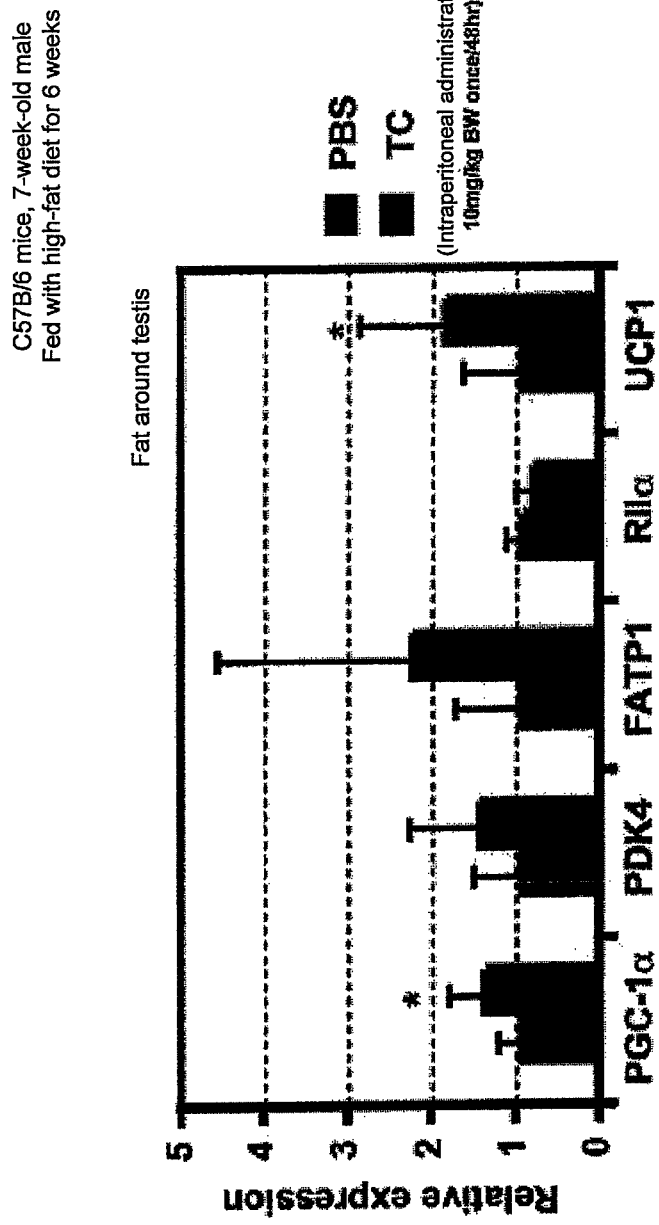
FIG. 7 shows the results of induction of the expression of a mitochondrial function gene group including PGC-1α in mice with the use of tranylcypromine.

(6) Activation of Expression of PGC-1α Gene and the Like by Administration of Tranylcypromine (FIG. 7)

C57B/6J mice (7-week-old male) were fed with high fat diet for 6 weeks, and at the same time, the mice were intraperitoneally administered with 10 mg/kg body weight tranylcypromine or PBS (n=8) every other day. Immediately before dissection, the mice were fasted for 16 hours, and tissues were then isolated from the mice. Using Trizol reagent (Invitrogen), total RNA was extracted from the white adipose tissues around testis and the liver of each mouse. Expression analysis was carried out as mentioned above. The expression level of PGC-1α or the like was standardized against the internal control gene 36B4. The value was given as a multiple of induction to a control mouse that had been treated with PBS.

Figure 8:
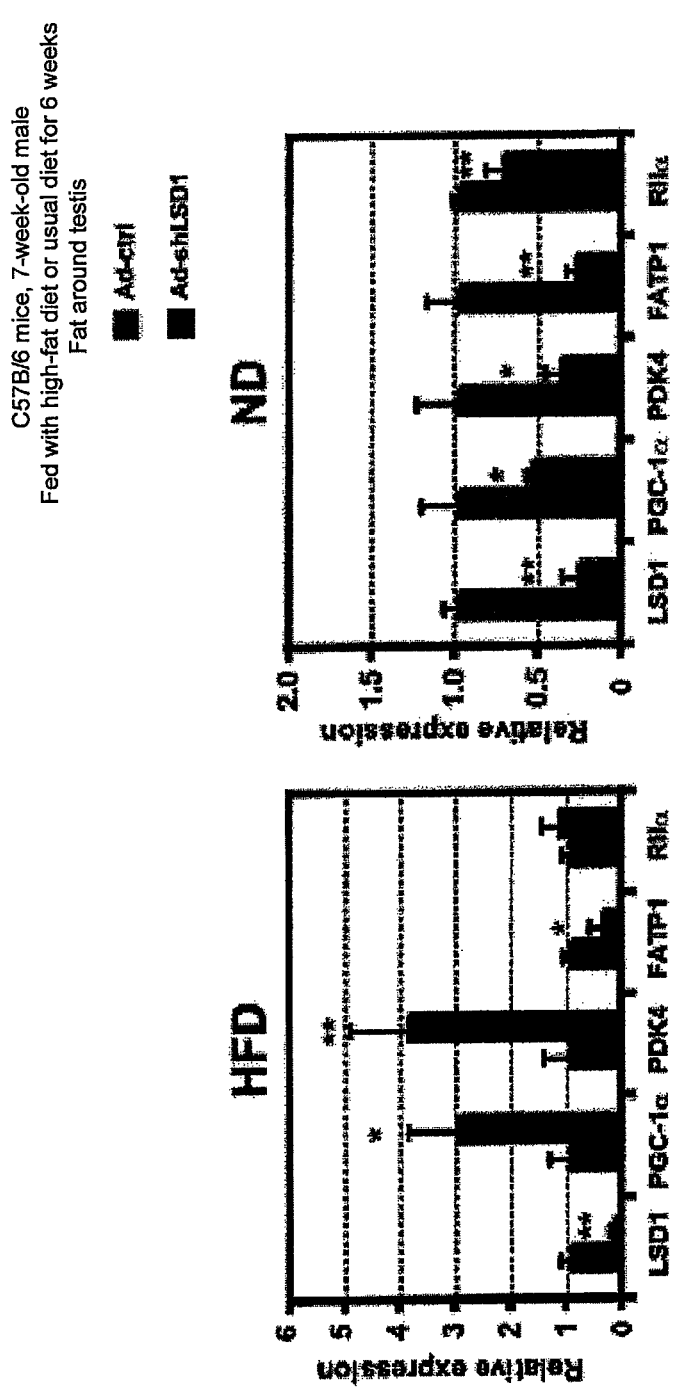
FIG. 8 shows the results of regulation of the expression of a mitochondrial function gene group including PGC-1α in mice by RNAi to LSD1.

(7) Regulation of Expression of PGC-1α Gene and the Like by Inhibition of LSD1 (FIG. 8)

C57B/6J mice (7-week-old male) were fed with high fat diet or usual diet for 6 weeks, and the white adipose tissues around the testis were then isolated from each mouse. Using an adenovirus vector, LSD1 shRNA was introduced into finely fragmented tissues, and total RNA was then extracted from the tissues using Trizol reagent (Invitrogen). Expression analysis was carried out as described above. The expression level of PGC-1α or the like was standardized against the internal control gene 36B4. The value was given as a multiple of induction to control tissues using a control adenovirus.

Figure 9:
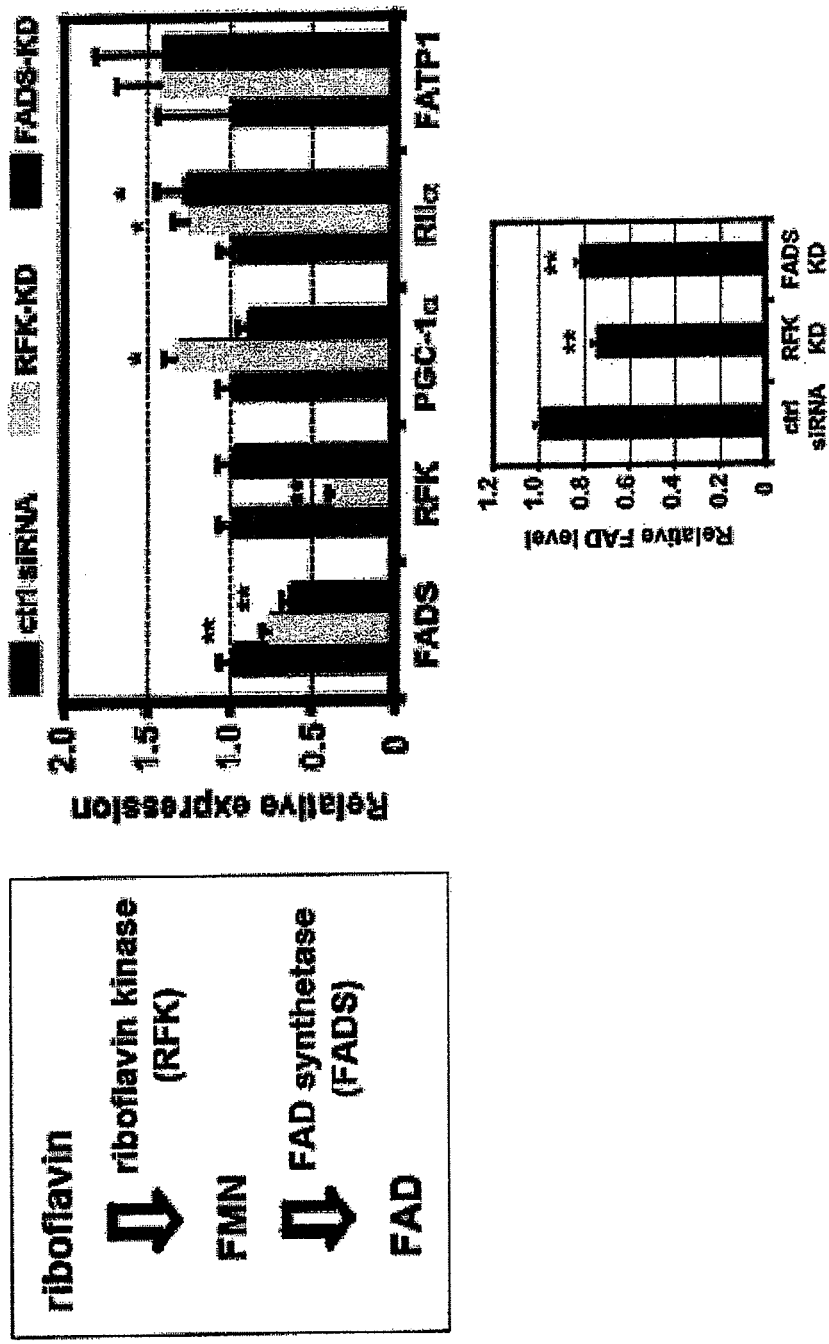
FIG. 9 shows the results of induction of the expression of an LSD1 target gene group (which is a mitochondrial function gene group including PGC-1α) by inhibition of an enzyme associated with flavin adenosine dinucleotide (FAD) synthesis.

(8) Induction of Expression of LSD1 Target Genes by Inhibition of Enzyme Associated with FAD Synthesis (FIG. 9)

Using Trizol reagent (Invitrogen), total RNA was extracted from 3T3-L1 cells in which siRNA against riboflavin kinase (RFK) or FAD synthase (FADS) had been introduced. Quantitative RT-PCR was carried out as described above, and the expression level of PGC-1α or the like was standardized against the internal control gene 36B4. The value was given as a multiple of induction to a sample into which control siRNA had been introduced, or a sample treated with a vehicle. Using FAD assay kit (BioVision), the amount of FAD in the cells was measured under inhibition of FAD synthesis.

Figure 10:
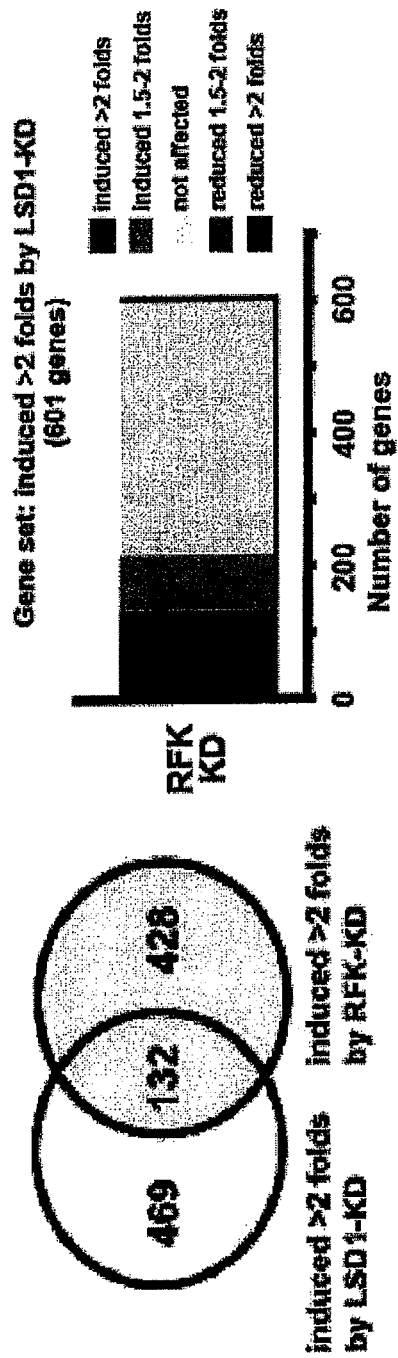
FIG. 10 shows the results of a comprehensive analysis of LSD1 target genes in 3T3-L1 cells, utilizing RNAi to LSD1 and RNAi to flavin adenosine dinucleotide synthase.

(9) Overlapping of Target Genes Regulated by LSD1 and FAD Synthase (FIG. 10)

After completion of the introduction of siRNA against RFK using RNAimax reagent (Invitrogen), 3T3-L1 cells were cultured in a differentiation induction medium for 24 hours. Thereafter, RNA analysis was carried out as described above. Using GeneChip Mouse Genome Array 430_2 in combination with GeneChip Hybridization, Wash and Stain Kit (Affymetrix), genome-wide expression analysis was carried out.

Figure 11:
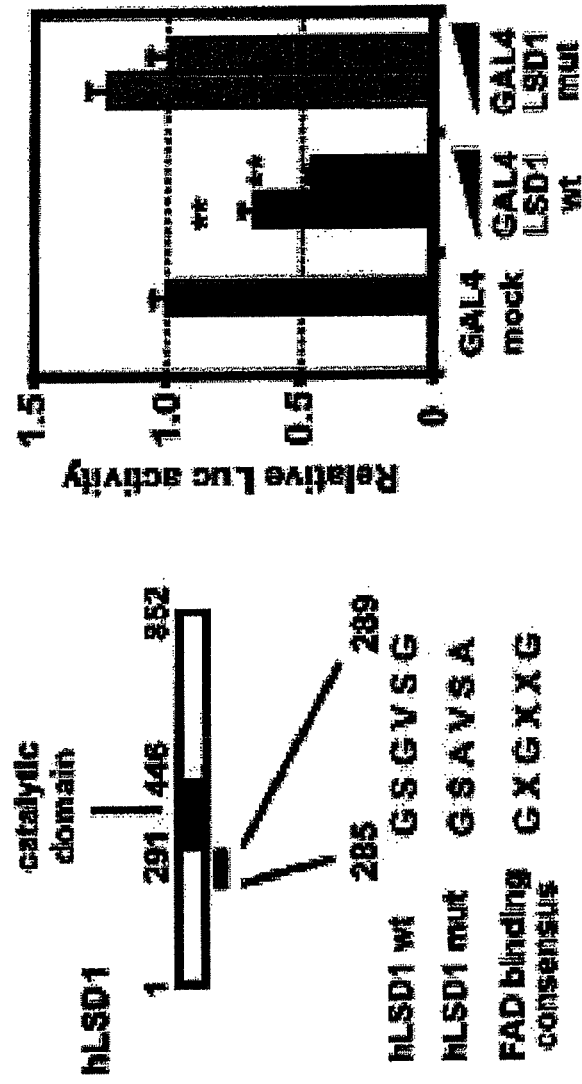
FIG. 11 shows the results of an analysis of flavin adenosine dinucleotide (FAD)-dependent transcription repression function of LSD1.

(10) FAD-Dependent Transcription Repression Function of LSD1 (FIG. 11)

Using a luciferase reporter vector containing a GAL4 binding sequence and a promoter, luciferase assay was carried out as described above, employing Dual-Luciferase Reporter Assay System (Promega). 3T3-L1 cells were co-transfected with this reporter vector and an expression vector containing LSD1 fused with GAL4 (a wild type or a loss-of-FAD-binding type), and luciferase activity was then measured.

Figure 12:
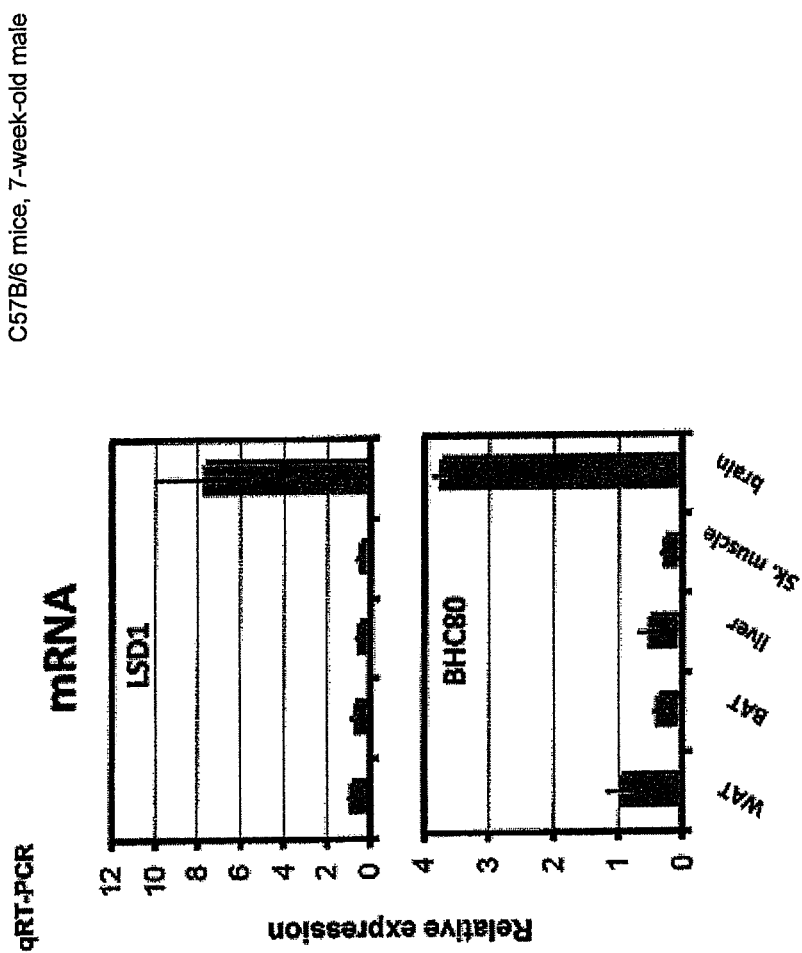
FIG. 12 shows the results of the expression status of LSD1 and BHC80 in mouse tissues.

(11) Expression of LSD1 and BHC80 in Mouse Tissues (FIG. 12)

Various tissues were isolated from C57B/6J mice (7-week-old male), and total RNA was then extracted using Trizol reagent (Invitrogen). The expression levels of LSD1 and BHC80 were each standardized against the internal control gene 36B4. The value was given as a multiple to white adipose tissues. WAT (white adipose); BAT (brown adipose); liver (liver); Sk.musde (skeleton muscle); and brain (brain).

Figure 13:
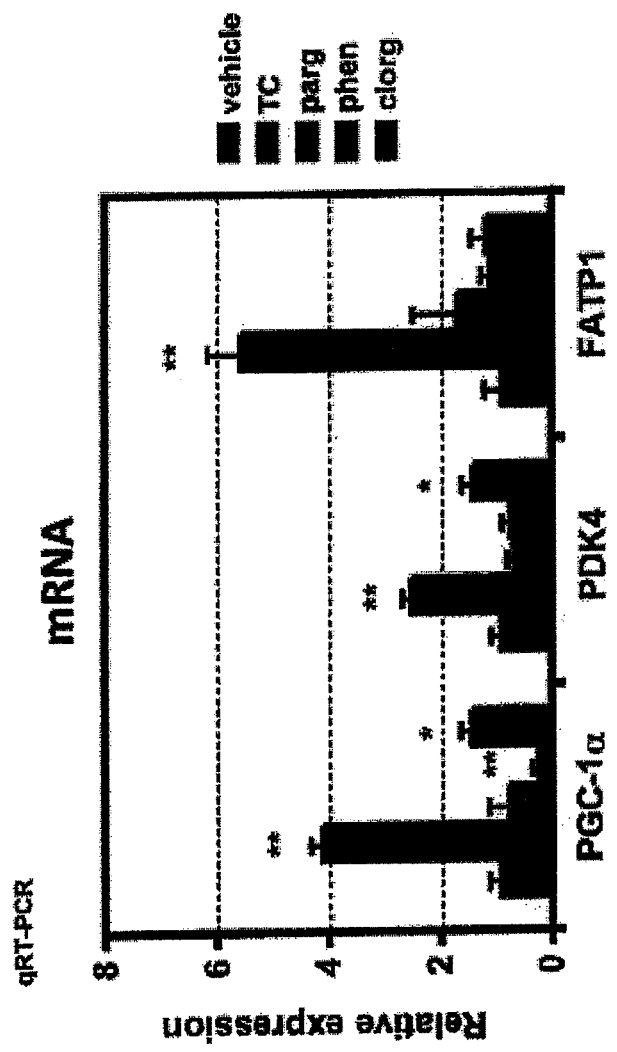
FIG. 13 shows the results of an analysis of the effects of main monoamine oxidase inhibitors on an LSD1 target gene group.

(12) Effects of Various Types of MAO Inhibitors on LSD1 Target Gene Group (FIG. 13)

After completion of the addition of tranylcypromine or monoamine oxidase (MAO) inhibitors, 3T3-L1 cells were cultured in a differentiation induction medium for 24 hours. Thereafter, RNA analysis was carried out. Expression analysis was carried out as described above. The expression level of PGC-1α or the like was standardized against the internal control gene 36B4. The value was given as a multiple of induction to a control treated with a vehicle. Tranylcypromine (TC), pargyline (parg), and phenelzine (phen) were each used in a concentration of $10^{-4}$ M. Clorgyline (clorg) was used in a concentration of $10^{-5}$ M.

(B) Results (1) Control of Energy Metabolism in Fat Cells by LSD1

Using siRNA or tranylcypromine (TC) that is a low molecular weight compound inhibitor, LSD1 function was eliminated from 3T3-L1 cells. Tranylcypromine has been first identified as an inhibitor of monoamine oxidase A and B (MAO A and B), and it has been biochemically demonstrated to have high specificity to inhibition of LSD1. Under such conditions, a comprehensive expression analysis was carried out using a microarray, and target genes were identified in differentiating 3T3-L1 cells (FIG. 1). There were 601 target candidates, which were matched with transcription repression activity of LSD1 and which were induced to a higher level (2-fold or more) by LSD1 knock-down (KD). The expression of a majority of the candidates was induced even by the coupling factor BHC80 knock-down (KD) or a tranylcypromine treatment (FIG. 1, upper view). Target genes, which were common in three groups, namely, LSD1 KD, BHC80 KD, and TC, contained a large number of key regulatory molecules for energy expenditure and mitochondrial biosynthesis, such as PGC-1α, pyruvate dehydrogenase kinase 4 (PDK4), and AMP-dependent protein kinase γ2 subunit (FIG. 1, lower table). Induction of the expression of genes such as PGC-1α by LSD1 or BHC80 knock-down (KD) and tranylcypromine was also confirmed by quantitative RT-PCR (FIG. 2).

(2) Epigenetic Regulation of PGC-1α Gene by LSD1

Whether or not a PGC-1α gene is directly regulated by H3K4 demethylation caused by LSD1 in 3T3-L1 cells was examined. As a result, it was demonstrated by chromatin immunoprecipitation (ChIP) analysis that, in cells in which LSD1 was knocked down, the amount of dimethylated H3K4 in a PGC-1α gene promoter was increased to a level approximately 2-fold higher than that of a control (FIG. 3). Such an increase in the amount of dimethylated H3K4 was detected even in a PGC-1α promoter under treatment with tranylcypromine (FIG. 3). The same results were obtained in the case of other LSD1 target gene promoters such as PDK4. In order to confirm the presence of LSD1 in a target promoter, this protein was subjected to ChIP analysis (FIG. 4). It was found that LSD1 was located near the transcription initiation site of the PGC-1α promoter (shown as site b). The same results were obtained in the case of other LSD1 target gene promoters. Moreover, the expression of a luciferase reporter gene located downstream of the PGC-1α promoter was activated (disinhibited) by LSD1 knock-down or a tranylcypromine treatment (FIG. 5).

(3) Activation of Mitochondrial Function by Inhibition of LSD1

Figure 6A:
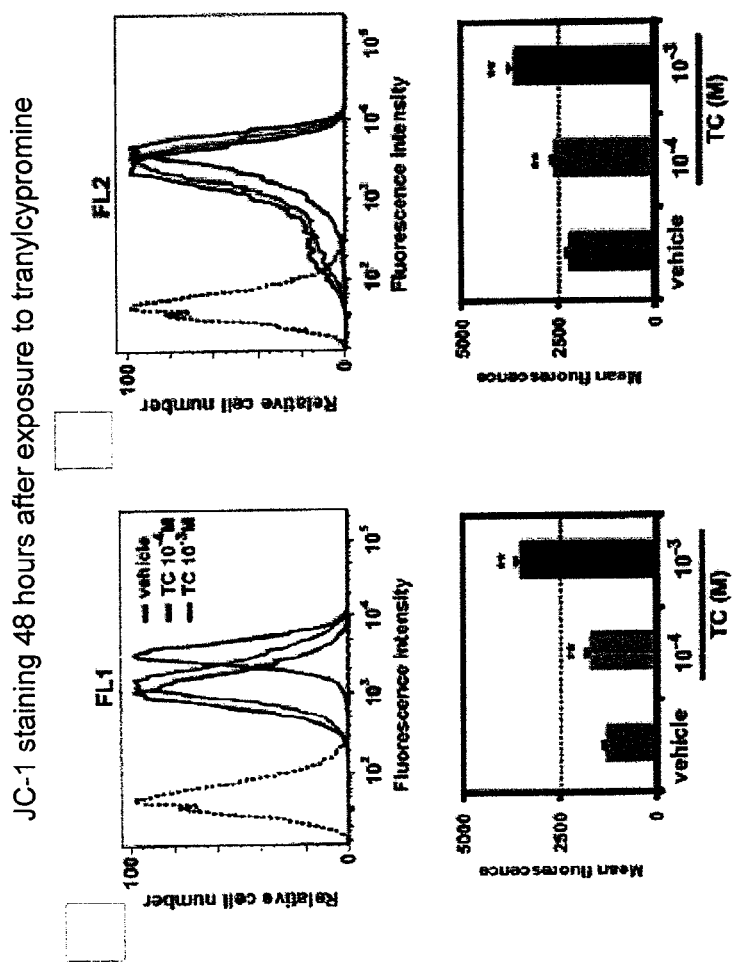
FIG. 6a shows the results of JC-1 staining 48 hours after the exposure of 3T3-L1 cells to tranylcypromine (TC).
Figure 6B:
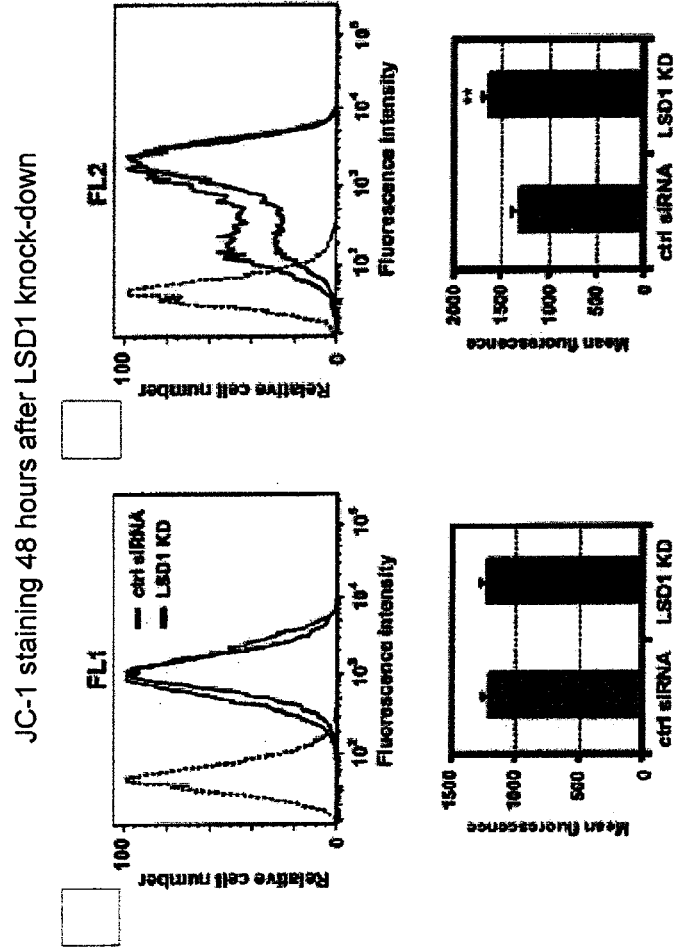
FIG. 6b shows the results of JC-1 staining after inhibition of LSD1.

In order to examine the cytological effect of energy expenditure that was reactivated under LSD1 inhibition conditions, the kinetics of mitochondrial function known to be activated by PGC-1α were examined. Tranylcypromine-treated cells were stained using JC-1 that is a fluorescent dye that binds to the mitochondrial inner membrane to emit green fluorescence (FL1; the amount of mitochondria) and forms a red fluorescence aggregate depending on membrane potential (FL2; mitochondrial activity) (FIG. 6a). As a result of flow cytometry analysis performed on JC-1-positive cells, it was found that tranylcypromine shows a stimulatory effect on both the amount of mitochondria and membrane potential. Moreover, the same results were obtained by LSD1 knock-down (FIG. 6b). These data show that LSD1 directly suppresses energy expenditure genes mediated by H3K4 demethylation and inhibits mitochondrial function. The data also show that mitochondrial function and energy expenditure can be activated by inhibition of LSD1.

(4) Induction of Expression of Mitochondrial Function Genes Including PGC-1α by Inhibition of LSD1 In Vivo Tranylcypromine is effective for the activation of mitochondrial function by inhibition of LSD1. Thus, whether or not the administration of tranylcypromine influences on energy homeostasis in vivo was examined. Seven-week-old C57B/6J mice were fed with high fat diet for 6 weeks, and at the same time, they were administered with 10 mg/kg body weight of tranylcypromine or PBS every other day. As a result of the administration of tranylcypromine, the expression of LSD1 target genes including PGC-1α was increased in fat around the testis of each mouse (FIG. 7). The same results as described above were obtained in the liver. These data show that energy expenditure is stimulated in vivo by the inhibition of LSD1 by tranylcypromine.

(5) Regulation of Expression of PGC-1α Gene and the Like by Inhibition of LSD1

In order to examine the significance of the improvement of energy expenditure, C57B/6J mice (7-week-old male) were fed with high fat diet or usual diet for 6 weeks. Thereafter, adipose tissues around the testis of each mouse were finely cut, and LSD1 was then inhibited by adenovirus vector-derived LSD1 shRNA. The expression level of PGC-1α or the like increased under high fat diet conditions, but it decreased under usual diet conditions (FIG. 8). These data show that inhibition of LSD1 regulates mitochondrial function, depending on energy state. That is to say, in the case of excessive energy intake, LSD1 inhibition promotes energy expenditure. On the other hand, in the case of ordinary energy intake, LSD1 inhibition suppresses energy expenditure. Thus, it is suggested that LSD1 inhibition maintains homeostasis in both cases.

(6) Induction of Expression of LSD1 Target Genes by Inhibition of Enzyme Associated with FAD Synthesis LSD1 is a FAD-dependent demethylase. Thus, the function of an intracellular FAD synthetic pathway was analyzed. With regard to this pathway, riboflavin kinase (RFK) and FAD synthase (FADS) are known as key enzymes (FIG. 9). When FAD synthesis was inhibited using siRNA against these enzymes, the expression of LSD1 target genes such as PGC-1α was activated. In addition, when FAD synthesis was inhibited, the amount of FAD in a cell decreased. These data suggest that LSD1 target genes can be activated by inhibition of FAD synthesis.

(7) Overlapping of Target Genes, the Expression of Each of which is Regulated by LSD1 and Enzyme Associated with FAD Synthesis In order to analyze target genes regulated by FAD, a comprehensive expression analysis was carried out using a microarray under conditions of the knock-down (KD) of LSD1 or RFK. As a result, such target genes were identified in 3T3-L1 cells (FIG. 10). In accordance with the transcription repression activity of LSD1, the expression of a majority of LSD1 target genes was also induced by RFK knock-down. These results demonstrated that target genes, the expression of each of which is regulated by LSD1 and the enzyme associated with FAD synthesis, are overlapped.

(8) FAD-Dependent Transcription Repression Function of LSD1

In order to examine the FAD dependency of LSD1 function, luciferase assay was carried out using a luciferase reporter vector containing a GAL4 binding sequence and a promoter (FIG. 11). When LSD1 fused with GAL4 was allowed to express, wild-type LSD1 suppressed transcription in an amount dependent manner. On the other hand, loss-of-FAD-binding-type LSD1 did not show such transcription repression ability. These data show that the transcription repression ability of LSD1 depends on FAD binding.

(9) Expression of LSD1 and BHC80 in Mouse Tissues

In order to examine the biological significance of LSD1, the expression of LSD1 and BHC80 in various types of tissues of mature mice was examined (FIG. 12). Among metabolic tissues, LSD1 and BHC80 were expressed at high levels in white adipose tissues. Also in brown adipose tissues, liver and skeleton muscle, they were expressed at moderate levels.

Moreover, LSD1 and BHC80 were expressed in brain tissues at extremely high levels. These results suggest that LSD 1 plays a certain role in energy metabolism of various tissues.

(10) Effects of Various Types of MAO Inhibitors on LSD1 Target Gene Group

The effects of tranylcypromine and the existing monoamine oxidases (MAO) on LSD1 target genes were analyzed (FIG. 13). When compared with pargyline (parg), phenelzine (phen), and clorgyline (clorg), tranylcypromine brought on significant activation of LSD1 target genes such as PGC-1α. Tranylcypromine has LSD1 inhibitory activity, and other MAO inhibitors have only low LSD1 inhibitory activity. Thus, these data support promotion of mitochondrial function genes by inhibition of LSD1, and at the same time, the data suggest that the LSD1 inhibitory effect can be distinguished from the MAO inhibitory effect.

The invention claimed is:

1. A method for improving mitochondrial function, which comprises administering a lysine-specific demethylase-1 (LSD-1) inhibitor, provided that tranylcypromine is excluded, to a subject, wherein the LSD-1 inhibitor is a nucleic acid capable of suppressing the expression of BHC80 or an enzyme associated with FAD synthesis by RNAi.

2. The method according to claim 1, wherein the enzyme associated with FAD synthesis is riboflavin kinase (RFK) and/or FAD synthase (FADS).

3. A method for improving mitochondrial function, which comprises administering a lysine-specific demethylase-1 (LSD-1) inhibitor, provided that tranylcypromine is excluded, to a subject, wherein the LSD-1 inhibitor is siRNA consisting of the sequence shown in SEQ ID NO: 29 and siRNA consisting of the sequence shown in SEQ ID NO: 30.

4. A method for inducing PGC-1α expression, which comprises administering a lysine-specific demethylase-1 (LSD-1) inhibitor, provided that tranylcypromine is excluded, to a patient, wherein the LSD-1 inhibitor is a nucleic acid capable of suppressing the expression of BHC80 or an enzyme associated with FAD synthesis by RNAi.

5. The method according to claim 4, wherein the enzyme associated with FAD synthesis is riboflavin kinase (RFK) and/or FAD synthase (FADS).

6. A method for inducing PGC-1α expression, which comprises administering a lysine-specific demethylase-1 (LSD-1) inhibitor, provided that tranylcypromine is excluded, to a patient, wherein the LSD-1 inhibitor is siRNA consisting of the sequence shown in SEQ ID NO: 29 and siRNA consisting of the sequence shown in SEQ ID NO: 30.

* * * * *